(12) United States Patent
Cowton et al.

(10) Patent No.: US 6,245,941 B1
(45) Date of Patent: Jun. 12, 2001

(54) REDUCTIVE ALKYLATION PROCESS FOR THE PREPARATION OF COMPOUNDS CONTAINING AT LEAST TWO AMINO GROUPS

(75) Inventors: Elizabeth L. M. Cowton, Warrington; Derek A. Bassett, Chester, both of (GB)

(73) Assignee: The Associated Octel Company Limited, London (GB)

(*) Notice: Subject to any disclaimer, the term of this patent is extended or adjusted under 35 U.S.C. 154(b) by 0 days.

(21) Appl. No.: 08/945,200

(22) PCT Filed: Apr. 12, 1996

(86) PCT No.: PCT/GB96/00894

§ 371 Date: Feb. 6, 1998

§ 102(e) Date: Feb. 6, 1998

(87) PCT Pub. No.: WO96/32371

PCT Pub. Date: Oct. 17, 1996

(30) Foreign Application Priority Data

Apr. 13, 1995 (GB) .................................... 9507659

(51) Int. Cl.⁷ ................................................. C07C 229/00
(52) U.S. Cl. ........................................ 562/565; 510/565
(58) Field of Search ............................. 562/565; 510/337

(56) References Cited

U.S. PATENT DOCUMENTS

| 4,704,233 | 11/1987 | Hartman et al. ................ 252/527 |
| 4,792,631 | 12/1988 | Mueller et al. ................. 564/489 |

(List continued on next page.)

FOREIGN PATENT DOCUMENTS

| 0 308 340 | 9/1988 | (EP) . |
| 0 634 485 A1 | 6/1994 | (EP) . |
| 57-058651 | 8/1982 | (JP) . |
| WO 92/09680 | 6/1992 | (WO) . |
| WO 94/03553 | 2/1994 | (WO) . |
| WO 94/03572 | 2/1994 | (WO) . |

OTHER PUBLICATIONS

J.C. Watkins; The Systhesis of Some Acidic Amino Acids Possessing Neuropharmacological Activity; Apr. 23, 1962.

*Primary Examiner*—Paul J. Killos
*Assistant Examiner*—Taylor V. Oh
(74) *Attorney, Agent, or Firm*—Sheridan Ross P.C.

(57) ABSTRACT

An alkylation process is described. The process comprises reacting at least a first nitrogen compound and a second nitrogen compound with a carbonyl compound in the presence of a reducing agent to form a product comprising at least two nitrogen groups; wherein the carbonyl compound comprises at least two carbonyl groups, the first nitrogen compound comprises a first nitrogen group reactive with one carbonyl group of the carbonyl compound and the second nitrogen compound comprises a second nitrogen group reactive with the other (or another) carbonyl group of the carbonyl compound, and wherein at least the first nitrogen compound or at least the second nitrogen compound comprises at least one other functional group. The process is especially suitable for the preparation of (S,S)-ethylenediaminedisuccinic acid (EDDS) of formula (1).

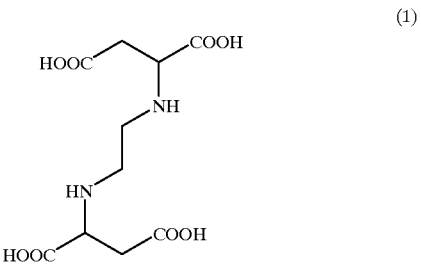

(1)

8 Claims, 1 Drawing Sheet

S,S-EDDS

U.S. PATENT DOCUMENTS

| | | | |
|---|---|---|---|
| 4,902,817 | | 2/1990 | Vincent et al. .................... 560/171 |
| 4,983,315 | * | 1/1991 | Glogowski et al. ............... 510/480 |
| 5,550,285 | * | 8/1996 | Layman, Jr. et al. ............. 562/565 |
| 5,587,512 | * | 12/1996 | Lin et al. ............................ 562/565 |
| 5,710,327 | * | 1/1998 | Kroner et al. ..................... 562/565 |
| 5,731,468 | * | 3/1998 | St. George et al. .............. 562/565 |
| 5,849,948 | * | 12/1998 | Patel et al. ........................ 562/565 |

\* cited by examiner

S,S-EDDS

S,S-EDDS

REDUCTIVE ALKYLATION PROCESS FOR THE PREPARATION OF COMPOUNDS CONTAINING AT LEAST TWO AMINO GROUPS

The present invention relates to an alkylation process. In particular, the present invention relates to a process for alkylating amino acids.

More in particular, the present invention relates to a process for the N-alkylation of amino acids, and especially a process for preparing (S,S)-ethylenediaminedisuccinic acid or a salt thereof.

Figure 1:
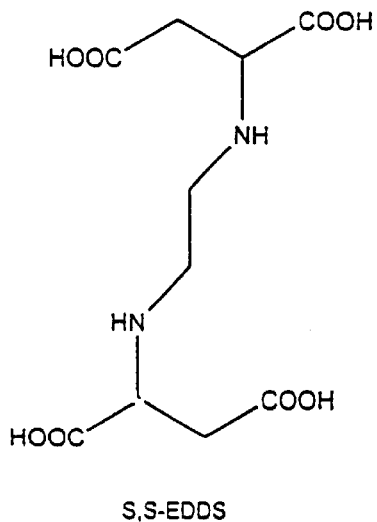

Certain compounds having amino acid moieties linked by a group joining their nitrogen atoms have a variety of uses mainly based on their metal chelating properties. Typical examples include their use as corrosion inhibitors, and in detergents, photographic developing solutions, rubber and resin formulations and metal treatments. One particular example is ethylenediaminedisuccinic acid ("EDDS") which has two chiral centres. The S,S-enantiomer of EDDS is preferred because of its biodegradability and its better chelating properties. EDDS is shown in FIG. 1.

Racemic EDDS is usually prepared by the reaction of maleic anhydride with ethylenediamine in NaOH solution, according to the procedure by W. M. Ramsey and C. Kerzerian of the Stauffer Chemical Company, U.S. Pat. No. 3,158,635. (S,S)-EDDS can be manufactured by a variety of different routes. A typical route is the reaction of NaOH with L-aspartic acid and dibromoethane following the protocol of Neal, J. A. and Rose, N. J. (Inorganic Chemistry, Vol. 7, No. 11, November 1968, pages 2405–2412, particularly page 2406). However, even though this synthetic route is the one that is typically used it is usually difficult to obtain economic yields of (S,S)-EDDS. Furthermore it is difficult to obtain highly pure (S,S)-EDDS.

The present invention seeks to overcome the problems associated with the known processes. In particular, the present invention seeks to provide a process that enables compounds like EDDS, more especially (S,S)-EDDS, to be prepared in high yields, economic yields and/or high purity.

According to the present invention there is provided an alkylation process comprising reacting at least a first nitrogen compound and a second nitrogen compound with a carbonyl compound in the presence of a reducing agent to form a product comprising at least two nitrogen groups; wherein the carbonyl compound comprises at least two carbonyl groups, the first nitrogen compound comprises a first nitrogen group reactive with one carbonyl group of the carbonyl compound and the second nitrogen compound comprises a second nitrogen group reactive with the other (or another) carbonyl group of the carbonyl compound, and wherein at least the first nitrogen compound or at least the second nitrogen compound comprises at least one other functional group.

There are a number of advantages associated with the present invention. For example, it enables compounds like EDDS, more especially (S,S)-EDDS, to be prepared in high yields. It also enables compounds like EDDS, more especially (S,S)-EDDS, to be prepared in economic yields. It also enables compounds like EDDS, more especially (S,S)-EDDS, to be prepared at a high purity. The present invention also provides a reliable process for preparing optically active compounds, such as (S,S)-EDDS, by use of a substantially aqueous reaction medium/media. Furthermore, the present invention provides a process that allows reduction in situ without requiring the need to isolate any intermediates in the reaction process. In some cases the intermediate or intermediates could be isolated, but preferably the intermediate or intermediates is/are not isolated.

In the process of the present invention the first nitrogen compound and/or the second nitrogen compound can comprise more than one additional nitrogen group, which need not be reactive with the carbonyl groups of the carbonyl compound. Also, in the process of the present invention an additional nitrogen compound or additional nitrogen compounds may be reacted. Also, an additional carbonyl compound or additional carbonyl compounds may be reacted, which carbonyl compound or carbonyl compounds can independently comprise one or more carbonyl groups. Also, a mixture of reducing agents may be used in the process of the present invention. In addition, at least the first nitrogen compound and/or at least the second nitrogen compound can comprise an additional functional group or additional functional groups. Other reactive compounds may be present in the reaction medium.

Preferably the first nitrogen group and the second nitrogen group are independently selected from a primary amine group or a secondary amine group.

Preferably each of the first nitrogen group and the second nitrogen group is a primary amine group, which may be the same or different.

Preferably the functional group is an acid group.

Preferably the acid group is a carboxylic acid group.

Preferably at least the first nitrogen compound or at least the second nitrogen compound comprises at least one chiral centre. More preferably at least the first nitrogen compound and at least the second nitrogen compound comprises at least one chiral centre.

Preferably the first nitrogen compound or the second nitrogen compound comprises 1–20 carbon atoms, more preferably 1–12 carbon atoms.

Preferably the first nitrogen compound or the second nitrogen compound is an amino acid.

Typical amino acids for use in the process of the present invention include any one or more of the 26 or so naturally occurring amino acids listed in standard textbooks, including the derivatives thereof. The amino acid may be any one or more of a "neutral" amino acid, a "basic" amino acid or an "acidic" amino acid. However, preferably the amino acid for use in the process of the present invention is not cysteine. This is because this amino acid has an -SH group which could undergo unwanted side reactions.

In the process of the present invention an amino acid having an α-amino group (e.g. aspartic acid) can be reacted. Alternatively, or in addition, in the process of the present invention an amino acid having a β-amino group (e.g. β-alanine) can be reacted.

Examples of neutral amino acids that may be used in the present invention include glycine, alanine, valine, leucine, norleucine, phenylalanine, tyrosine, serine, cystine, threonine, methionine, di-iodotyrosine, thyroxine, dibromotyrosine, tryptophan, proline and hydroxyproline.

Examples of basic amino acids that may be used in the present invention include ornithine, arginine, lysine and histidine.

Examples of acidic amino acids that may be used in the process of the present invention include aspartic acid, glutamic acid and β-hydroxyglutainic acid.

The preferred amino acids for the process of the present invention are those with two carboxyl groups and one amino group—i.e. the acidic amino acids listed above. Aspartic acid and glutamic acid are the most preferred of the three.

Specific optical isomers, particularly the L-form, are desirable because they increase biodegradability and in some cases, may also improve the chelating effect.

Preferably, therefore, the first nitrogen compound or the second nitrogen compound is an acidic amino acid.

Preferably the first nitrogen compound or the second nitrogen compound is aspartic acid.

Preferably the first nitrogen compound or the second nitrogen compound is an L-amino acid.

Preferably the first nitrogen compound or the second nitrogen compound is L-aspartic acid.

Alternatively, other amino acids may be reacted in the process of the present invention, such as D- or DL- amino acids, for example D-aspartic acid or DL-aspartic acid, to generate corresponding R,R- or racemic products having at least two nitrogen groups, such as R,R- or racemic EDDS.

Preferably the first nitrogen compound is the same as the second nitrogen compound.

Preferably at least one of the carbonyl groups of the carbonyl compound is an aldehyde group or a ketone group.

Preferably at least one of the carbonyl groups of the carbonyl compound is an aldehyde group or a ketone group, and wherein at least one other of the carbonyl groups of the carbonyl compound is an aldehyde group or a ketone group.

Preferably at least one carbonyl group is an aldehyde group.

Preferably the carbonyl compound comprises two carbonyl groups—i.e. the carbonyl compound is a di-carbonyl compound.

Preferably the carbonyl groups of the carbonyl compound are the same.

Preferably the carbonyl compound is a di-aldehyde.

Preferably the carbonyl groups of the carbonyl compound are attached to each other or to groups independently selected from any one of saturated or unsaturated, linear or branched or cyclic aliphatic groups (preferably $C_{1-20}$, more preferably $C_{1-12}$) or aromatic groups (preferably $C_{1-20}$, more preferably $C_{1-12}$). More preferably the at least two carbonyl groups of the carbonyl compound are attached to each other.

Preferably the carbonyl compound is glyoxal.

Preferably the reducing agent is any one of hydrogen and a hydrogenation catalyst, Zn/HCl, sodium cyanoborohydride, sodium borohydride, iron pentacarbonyl and alcoholic KOH, or formic acid, or combinations thereof.

The process of the present invention can be conducted at any appropriate pH condition.

Preferably, though, the process is conducted at a pH in the range of 7–14, more preferably in the range of 9–14 and even more preferably in the range 11–14. The pH may be maintained with alkali (i.e. a base), typically aq. NaOH solution, though a wide variety of water-soluble inorganic and organic bases may be used. In some instances, it will be desirable to add alkali during the reaction.

The reaction medium is normally wholly aqueous but the presence of other solvents such as ethanol is not excluded. In some circumstances, alkali (base) may be provided wholly or in part by other components of the reaction medium, particularly when the first nitrogen compound and/or the second nitrogen compound is(are) in salt form.

Typically the alkylated product will be generally less soluble than the starting reactants so that the reaction mixture can be diluted to a level at which remaining starting reactant or reactants is(are) soluble, followed by acidification and selective crystallisation of the desired product.

Preferably, therefore, the first nitrogen compound and the second nitrogen compound are reacted with the carbonyl compound in an alkaline medium.

Preferably the first nitrogen compound and the second nitrogen compound are reacted with the carbonyl compound before addition of the reducing agent.

Preferably the product comprising at least two nitrogen groups contains at least one chiral centre, preferably at least two chiral centres.

Preferably the carbonyl compound is prepared in situ in the reaction medium.

Preferably the product comprising at least two nitrogen groups is EDDS.

Preferably the product comprising at least two nitrogen groups is (S,S)-EDDS.

The product comprising at least two nitrogen groups may be prepared in salt form by the process of the present invention. Typically, though more preferred for the preparation of (S,S)-EDDS via the reaction of L-aspartic acid with glyoxal and subsequent reduction, the reaction solution of the present invention is preferably acidified with HCl to a pH of between 2 and 5, preferably 2–3 with cooling, for the desired product to crystallise out.

The following table presents some preferred parameters for the present invention.

| Parameters | General Range | Preferred Range |
| --- | --- | --- |
| Ratio of N1 + N2:CC:RA | 1:0.5–8:0.5–4 | 1:0.8–2:0.8–2 |
| pH | 6–14 | 11–14 |
| Reaction temperature | −5 to 65° C. | 5 to 40° C. |
| Reaction time | Up to 18 hrs | 10 min–3 hrs |
| Temperature of RA addition | −5 to 60° C. | 0 to 40° C. |
| Time of RA addition | 5 min–8 hrs | 15 min–4 hrs |

[N1 + N2 = first nitrogen containing compound plus second nitrogen containing compound; CC = carbonyl compound; RA = reducing agent.]

A preferred embodiment of the present invention relates to an alkylation process comprising reacting at least a first amino acid and a second amino acid with a carbonyl compound in the presence of a reducing agent to form a product comprising at least two nitrogen groups; wherein the carbonyl compound comprises at least two carbonyl groups.

With this preferred embodiment, the process of the present invention may include the reaction of an aldehyde or a ketone with an amine as defined in the claims in the presence of hydrogen and a hydrogenation catalyst, whereby reductive alkylation of ammonia or the amine (or reductive amination of the carbonyl compound) takes place. Other reducing agents can be used instead of hydrogen and a catalyst, such as Zn/HCl, sodium cyanoborohydride, sodium borohydride, iron pentacarbonyl and alcoholic KOH, and formic acid.

A highly preferred embodiment of the present invention relates to an alkylation process comprising reacting L-aspartic acid with glyoxal in the presence of a reducing agent to form (S,S)-EDDS.

Thus, with this highly preferred embodiment, the process of the present invention involves the reductive N-alkylation of amino acids with glyoxal (a dialdehyde) to form a derivative which contains two molecules of the amino acid, linked together through the two nitrogen atoms by an ethyl chain.

More specifically, the highly preferred process of the present invention involves reacting L-aspartic acid in aqueous alkaline media with glyoxal, a dialdehyde, to form the corresponding intermediate, which is subsequently reduced with sodium borohydride. From an economic viewpoint, unreacted L-aspartic acid can be recycled. The use of alternate reducing agents such as hydrogen/catalyst is more economically viable. The preferred order of addition is that of the glyoxal to the sodium L-aspartate, followed by the addition of the sodium borohydride. Further glyoxal and sodium borohydride may be added as required.

As mentioned above, the carbonyl compound can be prepared in situ in the reaction medium. In this regard, a primary alcohol may be oxidised to the corresponding aldehyde by use of a reduced copper catalyst. The primary alcohol could even be subjected to the catalysed reduction in the presence of an amine. The resultant aldehyde can then be reacted with an amine to form an N-alkylamine by hydrogenolysis (such as in situ hydrogenolysis) of the intermediate. These postulated reaction schemes are presented below:

| | | |
|---|---|---|
| $RCH_2OH$ | → | $RCHO + H_2$ |
| $RNH_2 + RCHO$ | → | $RNHCH(OH)R$ |
| $RNHCH(OH)R + H_2$ | → | $RNHCH_2R + H_2O$ | wherein R represents a suitable alkyl (which may be any one of saturated, unsaturated, unsubstituted, substituted, linear or branched) or aryl group (unsubstituted or substituted).

For the process of the present invention, the primary alcohol could be ethylene glycol which could be oxidised to glyoxal with the reduced copper catalyst. Further reaction with L-aspartic acid produces (S,S)-EDDS under the hydrogenolysis conditions.

Figure 2:
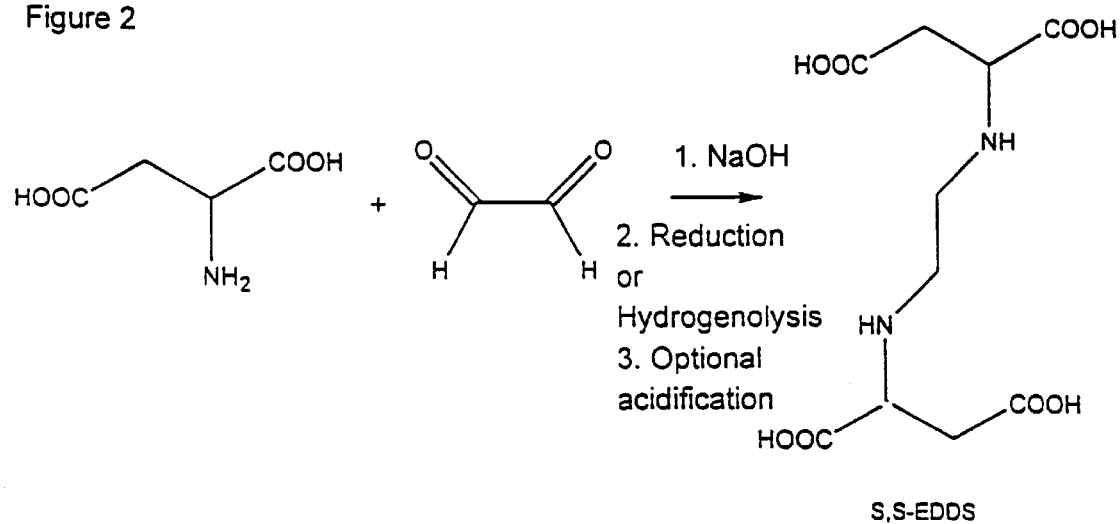

The present invention will now be described only by way of example, in which reference shall be made to the following Figures:

FIG. 1 is a representation of EDDS; and
FIG. 2 is a schematic representation of the preparation of EDDS by the process according to the present invention.

In the following examples, the term "conversion" refers to the weight of amino acid (i.e. the nitrogen compound) reacted (to form any product) divided by the weight of amino acid present initially ×100%. The term "selectivity" refers to the weight of amino acid reacted to form the desired product divided by the total amount of amino acid reacted ×100%.

EXAMPLE 1

L-Aspartic acid (5.26 g, 39.5 mmoles) was placed in a reaction flask, followed by distilled water (50 ml). The pH was adjusted to 11.6 with sodium hydroxide solution (6.31 g, 78.8 mmoles, 50% w/w) and glyoxal (5.71 g, 39.4 mmoles, 40 wt % solution in water) was added. After 15 minutes, the solution was cooled (ice/water bath) and sodium borohydride (1.69 g, 44.7 mmoles) was added portion-wise over 1.5 hours.

HPLC analysis after this time indicated a yield of 49% (2.81 g) (S,S)-ethylenediaminedisuccinic acid on L-aspartic acid.

Acidification of the solution to pH 2.7 with HCl resulted in the formation of solids. After 1 hour, the slurry was filtered and the solids were washed with water.

The mother liquors and washings were combined and the cake was slurried in water and basified to pH 9.5. HPLC analysis indicated that the mother liquors and washings contained 2.32 g L-asp and 0.14 g (S,S)-EDDS, and the cake contained 0.07 g L-asp and 2.6 g (S,S)-EDDS. This relates to an isolated yield of (S,S)-EDDS of 45%. The conversion of L-aspartic acid was 54.5% and the selectivity to (S,S)-EDDS was 87%. The general reaction scheme is shown in FIG. 2.

EXAMPLE 2

L-Aspartic acid (5.39 g, 40.5 mmoles) was placed in a reaction flask, followed by distilled water (50 ml). The pH was adjusted to 13.53 with sodium hydroxide solution (50% w/w) and glyoxal (5.89 g, 40.6 mmoles, 40 wt % solution in water) was added. After 15 minutes, the solution was cooled (ice/water bath) and sodium borohydride (1.74 g, 46 mmoles) was added portion-wise over 2 hours.

HPLC analysis after this time indicated a yield of 56% (S,S)-ethylenediaminedisuccinic acid on L-aspartic acid. Acidification with HCl to pH 2.6 afforded an isolated yield of 52% (S,S)-EDDS. The conversion of L-aspartic acid was 63% and the selectivity to (S,S)-EDDS was 90%. The general reaction scheme is shown in FIG. 2.

EXAMPLE 3

L-Aspartic acid (5.26 g, 39.5 mmoles) was placed in a reaction flask, followed by distilled water (50 ml). The pH was adjusted to 13.5 with sodium hydroxide solution (7.71 g, 96.4 mmoles, 50% w/w) and glyoxal (5.71 g, 39.4 mmoles, 40 wt % solution in water) was added. After 1 hour, the solution was cooled to 0° C. (ice/water bath) and sodium borohydride (1.68 g, 44.4 mmoles) was added portion-wise over 15 minutes. The temperature rose to 12° C. HPLC analysis after this time indicated a yield of 58.4% (3.37 g) (S,S)-ethylenediaminedisuccinic acid on L-aspartic acid. The conversion of L-aspartic acid was 70.5% and the selectivity to (S,S)-EDDS was 83%. The general reaction scheme is shown in FIG. 2.

EXAMPLE 4

The following table presents some preferred parameters for one aspect of the highly preferred embodiment of the present invention.

| Parameters | General Range | Preferred Range |
|---|---|---|
| Ratio of L-asp:glyoxal:NaBH$_4$ | 1:0.5–8:0.5–4 | 1:0.8–2:0.8–2 |
| pH | 6–14 | 11–14 |
| Reaction temperature | −5 to 65° C. | 5 to 40° C. |
| Reaction time | Up to 18 hrs | 10 min–3 hrs |
| Temperature of NaBH$_4$ addition | −5 to 60° C. | 0 to 40° C. |
| Time of NaBH$_4$ addition | 5 min–8 hrs | 15 min–4 hrs |

In summation, the present invention provides a novel and inventive process for preparing compounds such as EDDS, more especially (S,S)-EDDS. The process of the present invention is very different from the known reactions of glyoxal with an amino acid which have been described in gel formation reactions and to produce 'browning' in the food industry. The process of the present invention is very different from the known decarboxylation of an α-amino acid with glyoxal (i.e. Strecker degradation).

Other modifications of the present invention will be apparent to those skilled in the art.

What is claimed is:

1. An alkylation process comprising reacting at least a first nitrogen compound and a second nitrogen compound with a carbonyl compound in the presence of a reducing agent to form a product comprising at least two nitrogen groups; wherein said product is EDDS, the carbonyl compound is glyoxal, the first nitrogen compound is aspartic acid and the second nitrogen compound is aspartic acid.

2. A process according to claim 1 wherein said first nitrogen compound or said second nitrogen compound is L-aspartic acid.

3. A process according to claim 1 wherein said first nitrogen compound and said second nitrogen compound are reacted with said carbonyl compound in an alkaline medium.

4. A process according to claim 1 wherein said carbonyl compound is prepared in situ in said reaction medium.

5. An alkylation process comprising reacting at least a first nitrogen compound and a second nitrogen compound with a carbonyl compound in the presence of a reducing agent to form a product comprising at least two nitrogen groups;

wherein said product is (S,S)-EDDS;

the carbonyl compound is glyoxal, the first nitrogen compound is L-aspartic acid and the second nitrogen compound is L-aspartic acid.

6. A process according to claim 1 wherein the reaction medium is wholly aqueous.

7. A process according to claim 1 wherein the reducing agent is a member of the group consisting of hydrogen and a hydrogenation catalyst, Zn/HCl, sodium cyanoborohydride, sodium borohydride, iron pentacarbonyl and alcoholic KOH, formic acid, and any combinations of these reducing agents.

8. A process according to claim 1 wherein said first nitrogen compound and said second nitrogen compound are reacted with said carbonyl compound before addition of the reducing agent.

* * * * *